(12) United States Patent (10) Patent No.: US 8,211,313 B2
Fritchie et al. (45) Date of Patent: Jul. 3, 2012

(54) SYSTEM FOR PROCESSING MAGNETIC PARTICLES

(75) Inventors: Patrick P. Fritchie, Southlake, TX (US); Gregory E. Gardner, Grapevine, TX (US)

(73) Assignee: Abbott Laboratories, Abbott Park, IL (US)

( * ) Notice: Subject to any disclaimer, the term of this patent is extended or adjusted under 35 U.S.C. 154(b) by 27 days.

(21) Appl. No.: 12/643,376

(22) Filed: Dec. 21, 2009

(65) Prior Publication Data

US 2011/0147294 A1 Jun. 23, 2011

(51) Int. Cl.
*B03C 1/02* (2006.01)
*G01N 35/00* (2006.01)

(52) U.S. Cl. ......... 210/695; 210/222; 422/527; 436/526

(58) Field of Classification Search .................. 210/222, 210/695; 422/186.01, 527; 435/173.1; 436/526
See application file for complete search history.

(56) References Cited

U.S. PATENT DOCUMENTS

| | | | |
|---|---|---|---|
| 5,779,907 A * | 7/1998 | Yu | 210/695 |
| 5,795,784 A | 8/1998 | Arnquist et al. | |
| 5,856,194 A | 1/1999 | Arnquist et al. | |
| 7,556,770 B2 | 7/2009 | Justin et al. | |
| 7,572,638 B2 | 8/2009 | Pressman et al. | |
| 2002/0174878 A1 | 11/2002 | Nisson et al. | |
| 2003/0127396 A1* | 7/2003 | Siddiqi | 210/695 |
| 2007/0221543 A1 | 9/2007 | Karmeniemi et al. | |
| 2008/0308500 A1 | 12/2008 | Brassard | |
| 2009/0117004 A1 | 5/2009 | Fritchie et al. | |
| 2009/0117620 A1 | 5/2009 | Fritchie et al. | |
| 2009/0181359 A1 | 7/2009 | Lou et al. | |

FOREIGN PATENT DOCUMENTS

WO WO2009055442 A1 4/2009

OTHER PUBLICATIONS

International Search Report and Written Opinion for Application No. PCT/US2010/059899 mailed on Feb. 17, 2011, 12 pages.
Nook Industries: Linear Actutators for Motion Control Ball Screws, Screw Jacks, Lead Screws, Catalog [online], Nook Industries Inc., 2003, 2004, 2005, 2006, [retrieved on May 11, 2010]. Retrieved from the Internet: <URL: http://www.nookindustries.com/>, pp. 1-5.

* cited by examiner

*Primary Examiner* — David A Reifsnyder
(74) *Attorney, Agent, or Firm* — Hanley, Flight & Zimmerman, LLC.

(57) ABSTRACT

A system for separating a solid magnetic substrate from liquid contents of a reaction vessel, the system comprising at least one micro-well plate having a plurality of rows and a plurality of magnets arranged in at least two rows. In one embodiment, the at least two rows of the plurality of magnets are controlled so as to cause the magnets in the at least two rows of magnets to move in unison. In another embodiment, one row of the at least two rows of the plurality of magnets is controlled so as to cause the magnets in said one row to move at a first velocity in the vertical direction and another row of the at least two rows of the plurality of magnets is controlled so as to cause the magnets in that other row to move at a second velocity in the vertical direction.

16 Claims, 15 Drawing Sheets

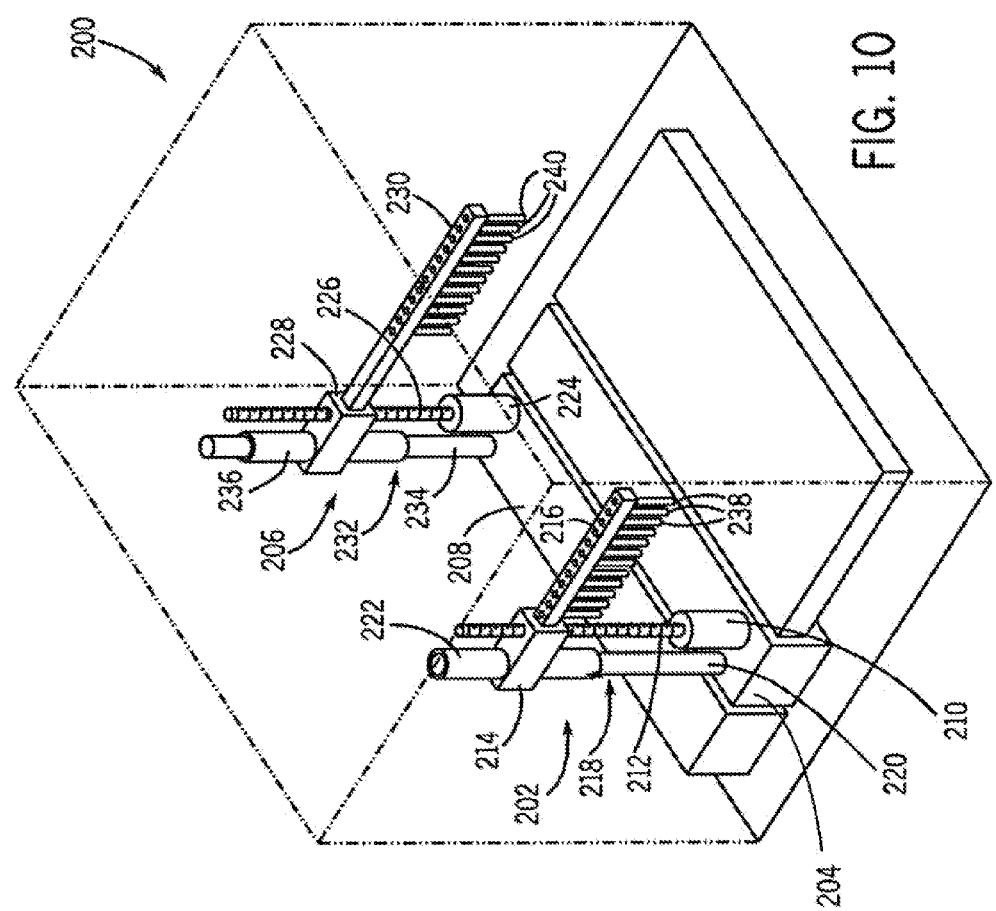

SYSTEM FOR PROCESSING MAGNETIC PARTICLES

BACKGROUND OF THE INVENTION

1. Field of the Invention

This invention relates to magnetic particle processing, and, more particularly, a system for inverse magnetic particle processing.

2. Discussion of the Art

Automated analyzers are well-known in the field of clinical chemistry and in the field of immunochemistry. Representative examples of such automated analyzers include, but are not limited to, PRISM® analyzers, AxSYM® analyzers, ARCHITECT® analyzers, all of which are commercially available from Abbott Laboratories, Cobas® 6000, commercially available from Roche Diagnostics, Advia, commercially available from Siemens AG, Dimension Vista, commercially available from Dade Behring Inc., Unicel® DxC600i, commercially available from Beckman Coulter Inc., and VITROS, commercially available from Ortho-Clinical Diagnostics. Each of these analyzers suffers from various shortcomings, some more than others. Some of the shortcomings encountered by more than one of these automated analyzers include the use of large volumes of sample, the use of large volumes of reagents, the generation of large volumes of liquid waste, and high costs. Some of the aforementioned automated analyzers require a great deal of maintenance, both scheduled and unscheduled. In addition, some of the aforementioned automated analyzers have scheduling protocols for assays that cannot be varied, i.e., the assay scheduling protocols are fixed, which limits such features as throughput.

Users of automated clinical analyzers desire to automate as many functions as possible. In the area of automated immunoassays, some of which require separation of reaction products from a reaction mixture in a reaction vessel, certain types of subsystems are necessary for separating a solid magnetic substrate from the liquid contents of a reaction vessel. These liquid contents can be unbound sample, unbound conjugate, wash buffer, a pre-trigger solution. Some automated immunoassay analyzers do not have the necessary versatility that would enable them to be used in systems that are designed to allow seamless integration with clinical chemistry analyzers. For example, magnetic separation of solid magnetic substrate from the liquid contents of a reaction vessel is difficult to integrate with clinical chemistry assays because of the need to use external magnets, washing mechanisms, in-track vortexers, inflexible process paths, and instantaneous dispensing of liquids at certain key points of immunoassay protocols.

Commercially available subsystems for separating a solid magnetic substrate from the liquid contents of a reaction vessel that do not have (a) an incubation capability integrated with such separating capability, (b) an automated interface for loading reaction vessels, and (c) radio frequency reading of radio frequency identification tags attached to reaction vessels are difficult to operate efficiently.

Magnetic separation of a solid magnetic substrate from the liquid contents of a reaction vessel can be carried out by a method known as inverse magnetic particle processing. The operating principle of inverse magnetic particle processing technology, commonly referred to as MPP, involves moving magnetic particles from one micro-well to another micro-well, e.g., from a micro-well in a given row and column of a micro-well plate to a micro-well in the same row and in another column of the micro-well plate, at least one micro-well in the micro-well plate containing reagent(s) required for the immunoassay, rather than moving liquids from one micro-well to another micro-well. This principle stands in contrast to the external magnet method, which is used in such automated analyzers as the ARCHITECT® analyzer, commercially available from Abbott Laboratories. According to inverse magnetic particle processing technology, magnetic particles are transferred with the aid of the magnetic rods covered with disposable, specially designed plastic tip combs.

Magnetic particle processors are commercially available under the trademarks KingFisher™ and KingFisher™ 96 from Thermo Fisher Scientific, Inc., Waltham, Mass. These magnetic particle processors are described, for example, in U.S. application Ser. No. 11/923,828, filed Oct. 25, 2007, and entitled METHOD OF PERFORMING ULTRA-SENSITIVE IMMUNOASSAYS, incorporated herein by reference.

Customers desire automated assays and throughput for these assays that are tailored to their requirements. However, subsystems for magnetic separation and mixing that are currently commercially available cannot be reconfigured and are not designed to have features that allow customization. In addition, customers desire to incorporate new assays into their automated analyzers without the need for changing the automated analyzers. Subsystems for magnetic separation and mixing are not designed to have features that support new assay protocols. Therefore, it would be desirable to develop a magnetic particle processor that would be sufficiently flexible to enable users of the magnetic particle processor to reconfigure the magnetic particle processor and to customize the magnetic particle processor for desired operations, so that new assays can be incorporated into an automated analyzer without the need for changing one magnetic particle processor for another.

SUMMARY OF THE INVENTION

In one aspect, this invention provides a system for separating a solid magnetic substrate from the liquid contents of a reaction vessel in an immunoassay. These liquid contents can be unbound sample, unbound conjugate, wash buffer, pre-trigger solution. In one embodiment, the system comprises a conventional inverse magnetic particle processor, such as, for example, an inverse magnetic particle processor commercially available from Thermo Fisher Scientific, Inc., Waltham, Mass., or the like, that has been modified to include additional sets of magnets in order to increase throughput. In another embodiment, the system comprises a conventional inverse magnetic particle processor, such as, for example, an inverse magnetic particle processor commercially available from Thermo Fisher Scientific, Inc., Waltham, Mass., or the like, that has been modified to vary the positioning of magnets. In still another embodiment, the system comprises a conventional inverse magnetic particle processor, such as, for example, an inverse magnetic particle processor commercially available from Thermo Fisher Scientific, Inc., Waltham, Mass., or the like, that has been modified in such a manner so as to enable variations of typical operations, e.g., mixing, washing, of inverse magnetic particle processing.

In one aspect, this invention provides a system for separating a solid magnetic substrate from liquid contents of a reaction vessel, the system comprising at least one micro-well plate having a plurality of rows and a plurality of magnets arranged in at least two rows.

In one embodiment, the at least two rows of the plurality of magnets are controlled so as to cause the magnets in the at least two rows of magnets to move in unison.

In another embodiment, one row of the at least two rows of the plurality of magnets is controlled so as to cause the magnets in said one row to move at a first velocity in the vertical direction and another row of the at least two rows of the plurality of magnets is controlled so as to cause the magnets in that other row to move at a second velocity in the vertical direction.

The system described herein combines magnetic separation, mixing, and washing functions with incubation functions, thereby providing a method for performing inverse magnetic particle processing protocols for immunoassays more effectively. The system allows automated immunoassay analyzers to be smaller, more reliable, and less complex than existing automated immunoassay analyzers, by combining two or more functions, by performing assays within a micro-well plate, and by using a XYZ aspirating/dispensing device to load micro-well plates into the inverse magnetic particle processor. Elimination of washing mechanisms, pumps for washing mechanisms, in-track vortexers, process paths, reaction vessel loaders, and the requirement of instantaneous reagent addition is brought about by using micro-well plates rather than the consumable items utilized by conventional automated immunoassay analyzers. The system described herein allows new assay protocols to be accommodated with minimal effect upon the design of the automated immunoassay analyzer by using a XYZ aspirating/dispensing device to automatically obtain access to micro-well plates for dispensing of liquids into micro-wells. The required control synchronization can be performed via a commercially available interface on the inverse magnetic particle processor, and a commercially available interface on the XYZ aspirating/dispensing device.

Inverse magnetic particle processing provides a micro-well plate format. Inverse magnetic particle processing eliminates the need for a process path of the type use in an ARCHITECT® analyzer, eliminates loaders for reaction vessels, eliminates mixers, and eliminates process path washing mechanisms, which typically operate in accordance with a fixed protocol. Inverse magnetic particle processing allows kitting and eliminates the need for time-dependent additions of critical reagents and other liquids.

The modifications to the conventional inverse magnetic particle processor described herein enable an increase in throughput. Certain embodiments of the inverse magnetic particle processor allow one row of magnets to operate under conditions different from those of another row of magnets. Such conditions include, but are not limited to, velocity of vertical movement of magnetic rods, vigorousness of mixing of reaction mixtures, duration of incubation periods, bypassing wash operations altogether, and movements for collecting particles.

The subsystem for magnetic separation and mixing can be configured for different throughputs and batch sizes. The subsystem for magnetic separation and mixing allows an automated analyzer to adapt to a variety of user environments/laboratories with minimal changes. The subsystem for magnetic separation and mixing allows new assay protocols and a multiplicity of micro-well plate protocols to be accommodated with minimum effect on the design of the automated analyzer.

Control synchronization for multiple micro-well plate operations can be performed via RS-232 interface on the subsystem for magnetic separation and mixing, and via a USB interface on the XYZ dispenser platform.

BRIEF DESCRIPTION OF THE DRAWINGS

FIG. 10 is a schematic view of an inverse magnetic particle processor, in perspective, wherein two rows of magnets are available for use with a given micro-well plate. However, one row of magnets can be operated independently of the other row of magnets.

DETAILED DESCRIPTION

Figure 1:
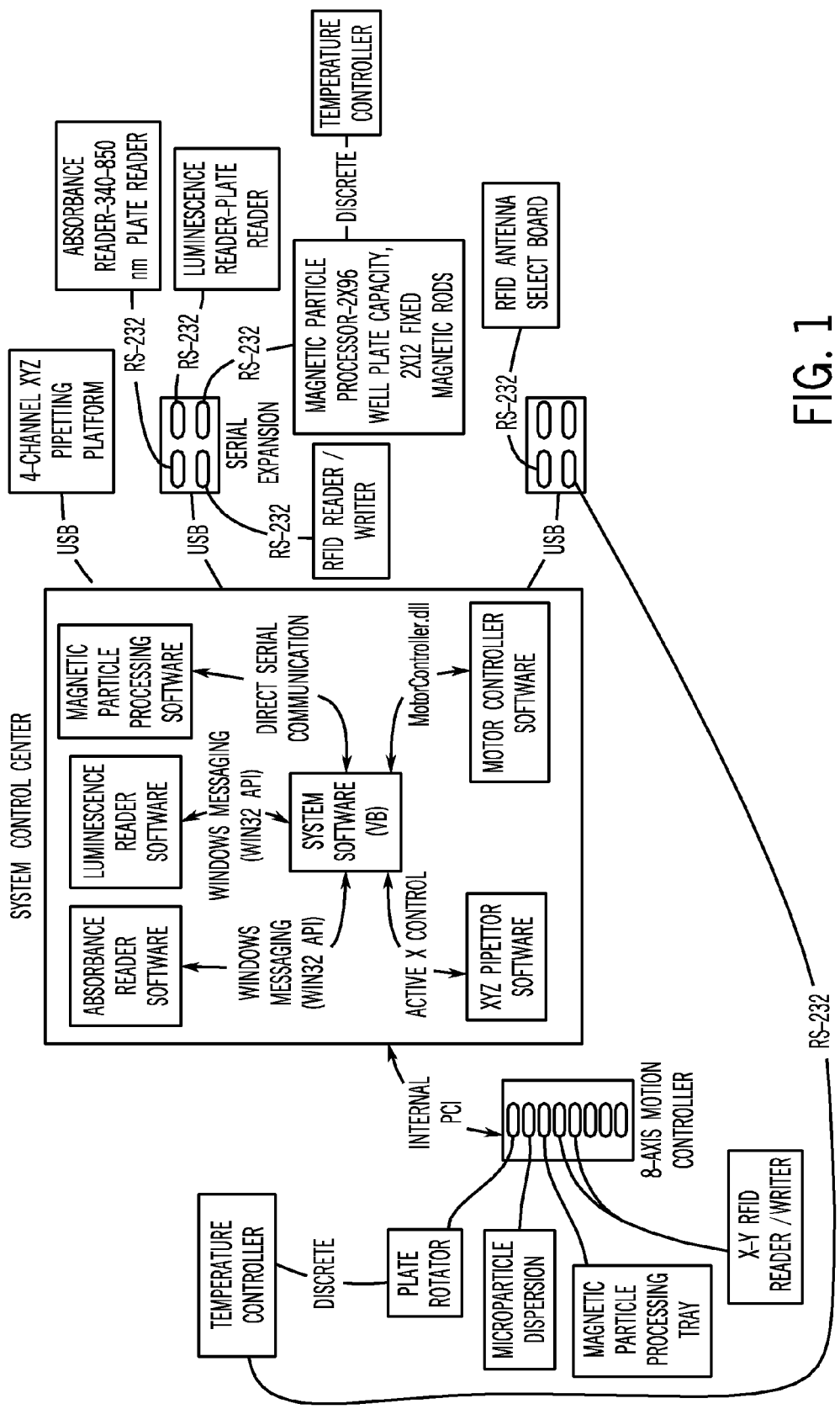
FIG. 1 is a schematic view of a computer interface suitable for providing control synchronization for the system described herein.

As used herein, the term "immunoassay" means a biochemical test that measures the concentration of a substance in a biological liquid, typically serum, using the reaction of an antibody or antibodies to its (their) antigen. An immunoassay takes advantage of the specific binding of an antibody to its antigen. As used herein, a "chemiluminescent microparticle immunoassay", alternatively referred to as "chemiluminescent magnetic immunoassay", involves a chemiluminescent label conjugated to the antibody or the antigen. In this assay, a magnetic microparticle is coated with antibodies. The assay is intended to look for antigens in the sample. A second antibody is labeled with a chemiluminescent label. This second antibody is not attached to a magnetic microparticle. The antibody and antigen with attach in the following order: antibody on magnetic microparticle-antigen-antibody-chemiluminescent label. The magnetic microparticle is then washed off. The amount of antibody-antigen-enzyme is measured by adding pre-trigger solution and trigger solution and measuring the light produced. This type of immunoassay produces light when combined with its substrate, i.e., a specific binding member. The chemiluminescent reaction offers high sensitivity and ease of measurement. This type of immunoassay involves a noncompetitive sandwich format that yields results that are directly proportional to the amount of analyte present in the sample. As used herein, the expressions "magnetic particle", "magnetic microparticle", or the like, means paramagnetic particle, magnetic microparticle, respectively, or the like.

As used herein, the term "sample" means a material suspected of containing an analyte. The sample can be used directly as obtained from the source in an assay or following a pretreatment to modify the character of the sample before undergoing an assay. The sample can be derived from any biological source, such as, for example, a physiological fluid, including, but not limited to, blood, saliva, ocular lens fluid, cerebral spinal fluid, sweat, urine, milk, ascites fluid, mucous, synovial fluid, peritoneal fluid, amniotic fluid, or the like. The sample can be pretreated prior to use, such as, for example, preparing plasma from blood, diluting viscous fluids, or the like. Methods of pretreatment can involve filtration, distillation, concentration, inactivation of interfering components, and the addition of reagents. Besides physiological fluids, other liquid samples can be used, such as, for example, water, food products, and the like. In addition a solid material suspected of containing the analyte can be used as the sample. As used herein, the term "analyte" refers to the compound or composition to be detected or measured.

As used herein, the expression "aspirating/dispensing device" means a device that has the dual functions of removing liquids from containers by suction and distributing portions of the liquids aspirated into containers, e.g., micro-wells of micro-well plates. An aspirating/dispensing device that is capable of being used for the system described herein is described in U.S. Pat. No. 7,033,543, incorporated herein by reference. As used herein, the term "pipette", also called "pipet", "pipettor", means a laboratory instrument used to transport a measured volume of liquid. As used herein, the expression "micro-well plate", also called "microtiter plate", "microplate", means a flat plate having a plurality of "micro-wells" used as small test tubes. As used herein, the term "XYZ" refers to a device that can move in three directions, a first horizontal direction, a second horizontal direction that is perpendicular to the first horizontal direction, and a third direction that is perpendicular to both the first horizontal direction and the second horizontal direction.

As used herein, the symbol "(s)" following the name of an item indicates that one or more of the subject items is intended, depending upon the context. As used herein, the term "kitting" means dispensing samples and reagents in appropriate micro-wells of a micro-well plate prior to commencing chemical reactions.

Throughout the specification, so far as possible, like parts or components will have the same reference numerals; like parts or components may have different reference numerals when required for the sake of clarity. For example, FIG. 6 and FIG. 8 employ the same reference numerals as does FIG. 2.

The system described herein provides a subsystem for separating a solid magnetic substrate from the liquid contents of a reaction vessel in an immunoassay analyzer, i.e., a magnetic particle processor, to obtain direct access to a XYZ aspirating/dispensing device. Micro-well plates can be automatically inserted into and removed from the magnetic particle processor associated with the aforementioned subsystem. In addition, supplies for use in the magnetic particle processor can be automatically loaded onto and unloaded from certain mechanical components of the magnetic particle processor of the aforementioned subsystem.

The system can read radio frequency identification tags attached to a micro-well plate. The magnetic particle processor can also be used as an incubator/mixer for immunoassays that do not utilize magnetic microparticles. See, for example, U. S. Patent Application Publication No. 2009-0117620-A1 and U. S. Patent Application Publication No. 2009-0117004-A1, both of which are incorporated herein by reference.

Figure 2:
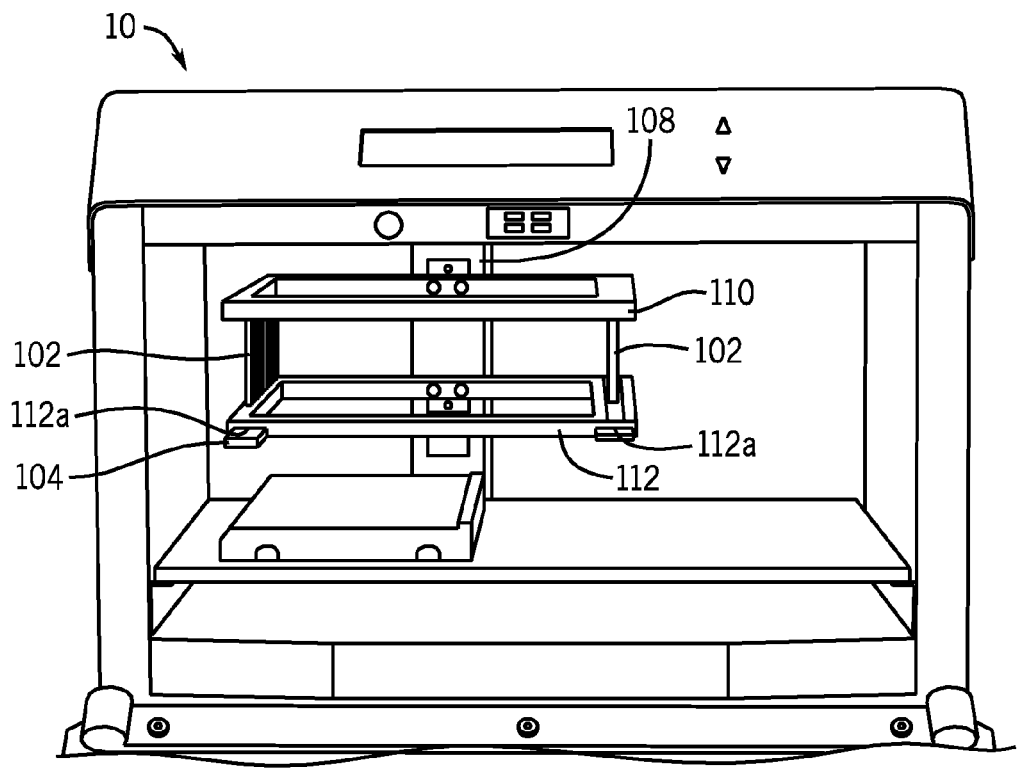
FIG. 2 is a front view in elevation of a commercially available inverse magnetic particle processor having one row of magnets for each micro-well plate.

The immunoassay processor(s) described herein provides (provide) the following functions: incubation of reaction mixtures, mixing of reaction mixtures, separation of components from reaction mixtures, washing of reaction product(s), and release of label to enable reading of the results of immunoassays. An immunoassay processor that can be modified for use herein is a KingFisher™ magnetic particle processor, commercially available from Thermo Fisher Scientific, Inc., Waltham, Mass., and described in U.S. application Ser. No. 11/923,828, filed Oct. 25, 2007, and entitled METHOD OF PERFORMING ULTRA-SENSITIVE IMMUNOASSAYS, incorporated herein by reference. This type of immunoassay processor is depicted in FIG. 2 and designated by the reference numeral 10. In the embodiment wherein the label is a chemiluminescent label, the release of label is carried out in a manner similar to that used in the ARCHITECT® analyzer, as described in U.S. Pat. Nos. 5,795,784 and 5,856,194, both of which are incorporated herein by reference. The trigger solution is dispensed during the reading of a reaction product in a well. Other magnetic particle processors that can be modified for use in certain embodiments described herein include KingFisher™ 96 magnetic particle processor, commercially available from Thermo Fisher Scientific, Inc., Waltham, Mass.

A synchronization controller is required in order to coordinate the movements of the XYZ aspirating/dispensing device, the magnetic particle processor, and the robot for transporting micro-well plates; the synchronization controller can be a RS-232 interface on the magnetic particle processor, and a USB interface on the XYZ aspirating/dispensing device. These interfaces are illustrated schematically in FIG. 1. Micro-well plates can be automatically loaded and unloaded by means of gripping devices on the pipettes of the XYZ aspirating/dispensing device.

Figure 3:
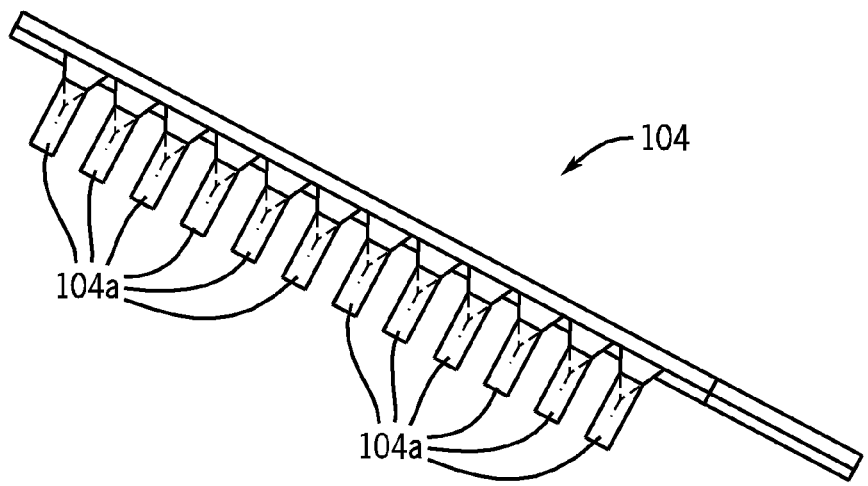
FIG. 3 is a front view in elevation of a tip comb suitable for use in the inverse magnetic particle processor shown in FIG. 2.

Referring now to FIGS. 2 and 3, the principle of the operation of an inverse magnetic particle processor 10 is based on the use of (a) magnetic rods 102 that can be covered with the tips or sheaths of disposable tip combs 104 and (b) micro-well plates. New tip combs 104 are installed in the inverse magnetic particle processor 10 prior to processing each micro-well plate (not shown). A tip comb 104 comprises a strip of non-magnetic material that joins a plurality of tips 104a, or sheaths, made of non-magnetic material, which tips, or sheaths, cover the magnetic rods 102. Commercially available tip combs 104 comprise twelve tips 104a, as shown in FIG. 3, for an inverse magnetic particle processor that processes twelve samples simultaneously and 96 tips for an inverse magnetic particle processor that processes 96 samples simultaneously.

Figure 6:
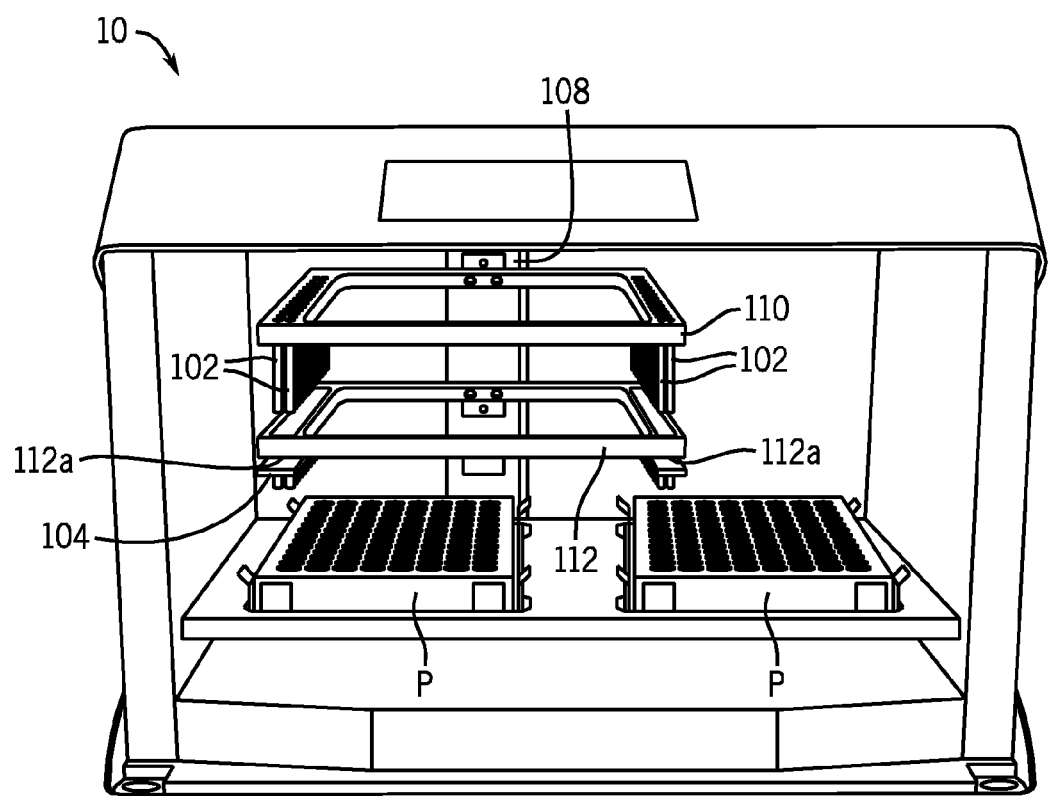
FIG. 6 is a front view in elevation of an inverse magnetic particle processor wherein two rows of magnets are available for use with a given micro-well plate.
Figure 8:
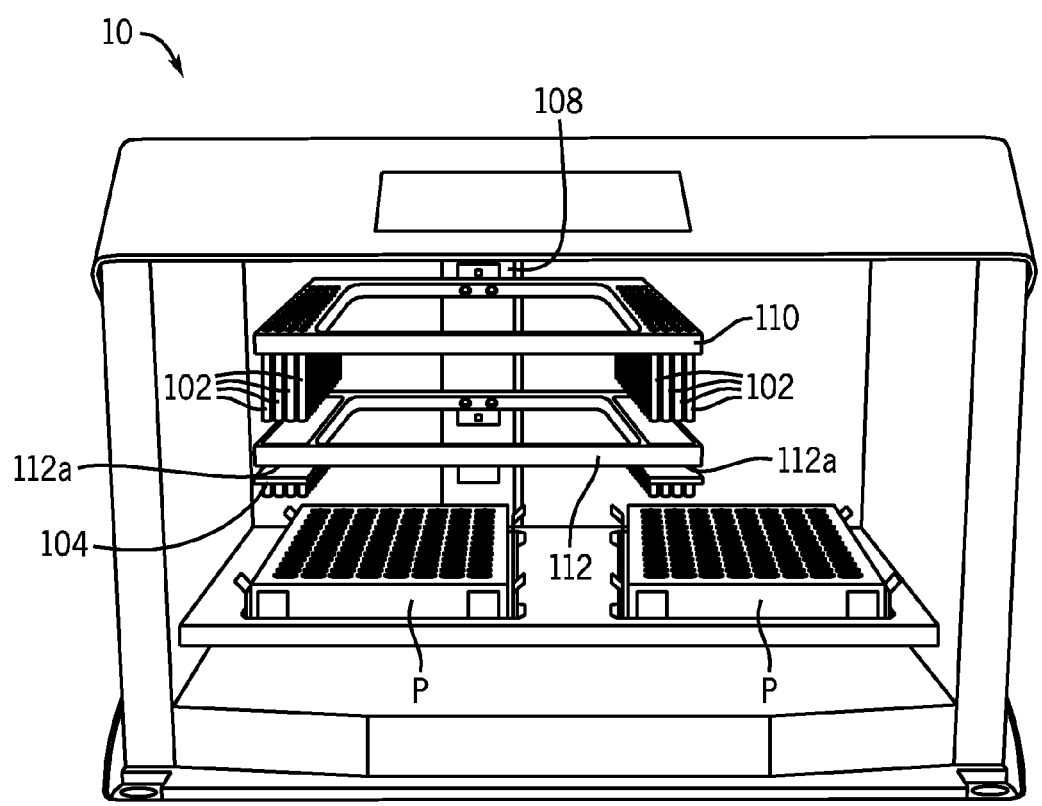
FIG. 8 is a front view in elevation of an inverse magnetic particle processor wherein four rows of magnets are available for use with a given micro-well plate.

The magnetic particle processor 10 is capable of carrying out magnetic particle processing steps without any aspirating and/or dispensing devices during magnetic particle processing. The magnetic particle processor 10 is designed for a maximum of two micro-well plates, each of which has 96 micro-wells. Micro-well plates are not shown in FIG. 2. However, micro-well plates are shown in FIG. 6 and FIG. 8 and are designated by the letter "P". The micro-well plates shown in FIG. 6 and FIG. 8 can be used in the magnetic particle processor shown in FIG. 2. The micro-well plates "P" are compatible with the tip combs 104. The micro-well plates are maintained stationary and the only moving assembly is a processing head 108 with tip combs 104 and magnetic rods 102. The processing head 108 consists of two vertically moving platforms 110, 112. One platform 110 is needed for the magnetic rods 102 (2×12 rods) and the other platform 112 is needed for the plastic tip combs 104 (2×12 tip combs). The platforms are rectangular metal frames that can be moved in both a horizontal direction, to move from one micro-well to another, and in a vertical direction to enter or exit a micro-well and to agitate magnetic particles in a micro-well. The platforms 110 and 112 are shown in FIG. 2. The additional row at the extreme right end of the platform 110 and the platform 112 can contain twelve (12) rods 102 and twelve (12) tip combs, respectively. This particular additional row has the function of processing magnetic particles on an adjacent micro-well plate "P". The additional rows at the extreme right end of the platforms 110 and the platform 112 do not process magnetic particles on the same micro-well plate "P".

A single micro-well plate contains twelve columns and eight rows of micro-wells and processing of one sample typically uses up to eight micro-wells of a given row. In certain embodiments two micro-well plates can be employed, whereby more than eight micro-wells can be used to carry out an immunoassay. One tip comb 104 containing twelve tips is used for processing twelve samples at a time within one micro-well plate, each sample requiring a separate column.

The dimensions of the micro-wells are compatible with the dimensions of the tip comb 104 and the tips, or the sheaths, thereof, with the result that the tips can be used to mix or agitate the contents of the micro-well. A single sample processing for an immunoassay can be carried out in a single micro-well plate containing ninety-six (96) micro-wells.

The operating principle employed by the magnetic particle processor is inverse magnetic particle processing technology, commonly referred to as MPP. Rather than moving liquids from one micro-well to another micro-well, the magnetic particles are moved from one micro-well to another micro-well, e.g., from a micro-well in a given column and row of a micro-well plate to a micro-well in the same column and in another row of the micro-well plate, at least one micro-well containing reagent(s) required for the immunoassay. This principle stands in contrast to the external magnet method, which is used in such automated analyzers as the ARCHITECT® analyzer, commercially available from Abbott Laboratories, Abbott Park, Ill. According to inverse magnetic particle processing technology, magnetic particles are transferred with the aid of the magnetic rods 102 covered with the disposable, specially designed plastic tip combs 104.

Figure 4:
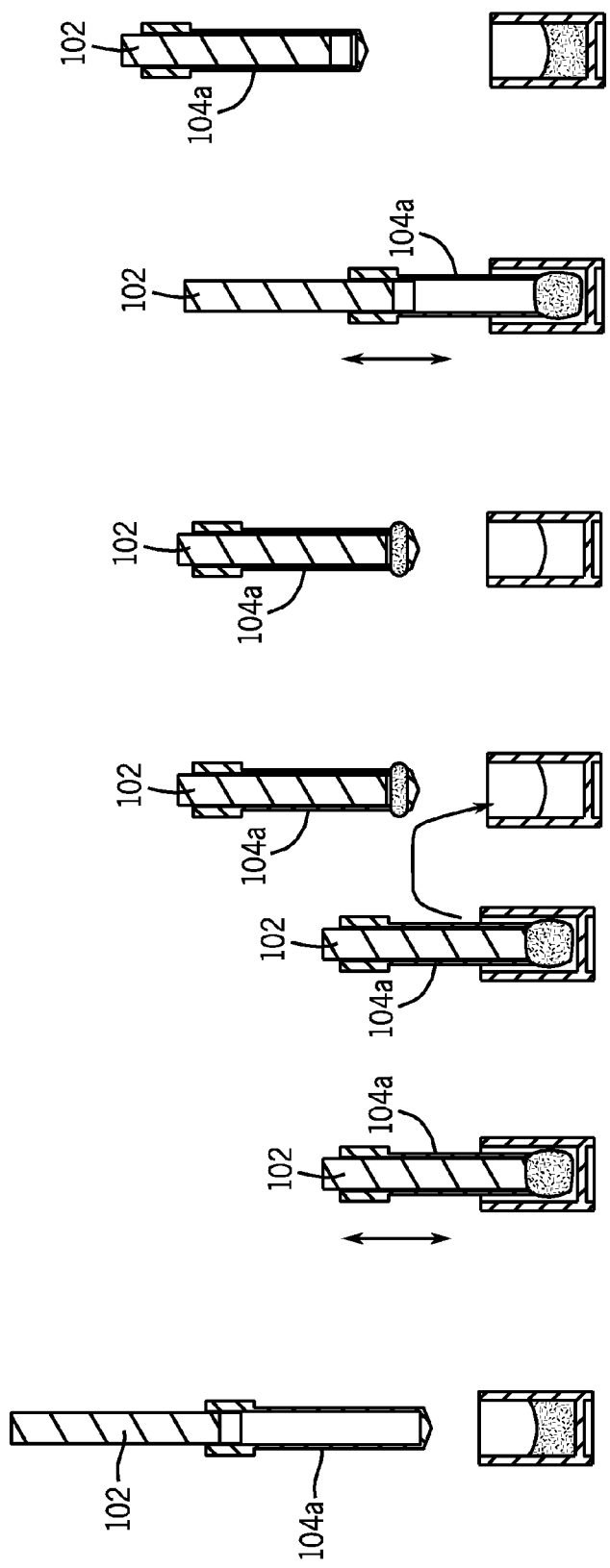
FIGS. 4A, 4B, 4C, 4D, 4E, and 4F are schematic diagrams illustrating a basic process that can utilize the principles of a KingFisher™ magnetic particle processor to process immunoassay reactions.
Figure 5:
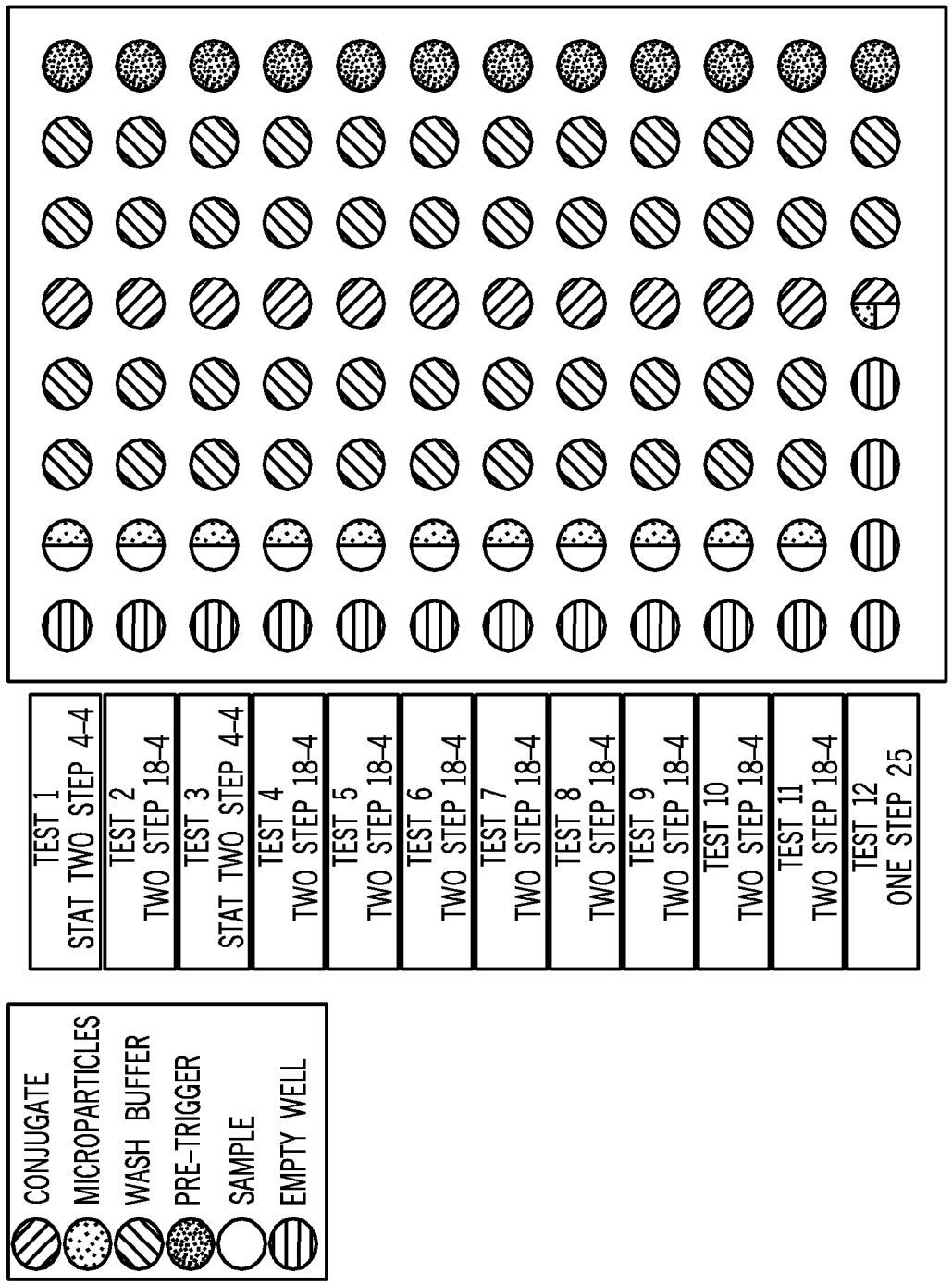
FIG. 5 is a top plan view of a micro-well plate illustrating the kitting of chemiluminescent microparticle immunoassays utilizing a single micro-well plate having 96 micro-wells. One row of micro-wells is processed at a time, and the entire protocol is carried out in a single micro-well plate.

FIGS. 4A, 4B, 4C, 4D, 4E, and 4F illustrate schematically basic elements of the inverse magnetic particle processing. FIG. 4A shows a suspension of magnetic particles in a micro-well before collection. FIG. 4B shows the collection of magnetic particles. FIG. 4C shows the transfer of magnetic microparticles from one micro-well to another micro-well. FIG. 4D shows the magnetic particles on the surface of a tip of the tip comb. FIG. 4E shows the release of magnetic particles in the micro-well. FIG. 4F shows a suspension.

Working with magnetic particles can be divided into at least six separate process steps:

Collecting particles: In this step, magnetic particles are collected from the micro-well specified.

Binding particles: In this step, material is collected onto the magnetic particles from the reagent in a specific micro-well.

Mixing particles: In this step, the reagent and particles (if inserted), are mixed with the plastic tip in a specific micro-well.

Releasing particles: In this step, the collected material is released from the surfaces of the magnetic particles into a specific micro-well.

Washing particles: In this step, the magnetic particles are washed in a specific micro-well.

Incubation of reaction mixtures: In this step the temperature of the reaction mixture is elevated to a sufficient level to obtain a satisfactory specific binding reaction. This step can be carried out at the same time as are the five steps listed previously.

During the collection of the magnetic particles from the micro-wells of a micro-well plate, the magnetic rods 102 are fully enclosed by the tips, or the sheaths, of the tip comb 104. The magnetic rods 102 together with the tip comb 104 move slowly up and down in the micro-wells, and the magnetic particles are collected onto the walls of the tips, or the sheaths, of the tip comb 104. The magnetic rod 102 together with the tip comb 104, having collected the magnetic particles, can be lifted out of one column of micro-wells and transferred into the next column of micro-wells required by the process, etc. After collection of the magnetic particles, the magnetic rods 102 together with the tip comb 104 are lifted from the micro-wells, the magnetic rods 102 are lifted out of the tips, or the sheaths, and the tips, or the sheaths, of the tip comb 104 are lowered into the next micro-well containing a reagent. Magnetic particles are released by moving the tip comb 104 up and down several times at considerably high velocity until all the particles have been mixed with the contents located in the succeeding row of micro-wells of the micro-well plate. This process can be carried out for twelve (12), twenty-four (24), forty-eight (48), or ninety-six (96) immunoassay reactions simultaneously.

Washing the magnetic particles is a frequent and an important phase of the magnetic particle processing activity. Washing is a combination of the release step and the collection step in a micro-well filled with a washing solution. To maximize washing efficiency in the micro-wells of a micro-well plate, the magnetic rods 102 together with the tip comb 104 are designed to have minimized liquid-carrying properties. To keep the suspension containing the magnetic particles evenly mixed in long-running reactions, the tip comb 104 can be moved up and down from time to time.

It is desired to have the temperature of the liquid in a micro-well in a micro-well plate to be at temperature of 37° C. during the time required to kit the micro-well plate for an immunoassay. In summary, the temperature of the kitting area (not shown) will be set (via RS-232 interface) so that the final temperature of the first liquids dispensed into the micro-wells of the micro-well plate reaches a temperature of 37° C. in the time required to dispense the remaining liquids. In other words, the liquids wherein temperature is critical are dispensed first. During magnetic particle processing, the temperature of the liquids within the micro-well plates "P" should be maintained at a temperature of 37° C. Proper maintenance of the temperature during magnetic particle processing can be ensured by the use of heater pads and the insulation of the magnetic particle processor 10. See, for example, U. S. Patent Application Publication No. 2009-0117004-A1, incorporated herein by reference. Similarly, the heater pads and the insulation in the magnetic particle processor 10 ensure proper maintenance of the temperature of the liquids within the micro-well plates "P" during magnetic particle processing.

United States Patent Application Publication No. 2009-0117004-A1, incorporated herein by reference, discloses how the tip comb platform 112 can be loaded with tip combs 104 by means of tip comb racks as the supporting tray for the micro-well plate(s) "P" moves into and out of the magnetic particle processor. The inverse magnetic particle processor comprises the same or a substantially similar processing head with tip combs and magnetic rods as shown in the magnetic particle processor shown in FIG. 2. As indicated with respect to FIG. 2, the processing head consists of two vertically moving platforms. One platform is needed for the magnetic rods (2×12 rods) and the other platform is needed for the plastic tip combs 104 (2×12 tip combs). The position of a tip comb slot 112*a* of the tip comb platform 112 of the inverse magnetic particle processor 10 is coordinated with the tip comb movements of the tip comb racks. A detailed discussion of the operation of the magnetic particle processor shown in FIG. 2 can be found in United States Patent Application Publication No. 2009-0117004-A1, previously incorporated herein by reference.

Dispensing of liquids into the micro-wells in a micro-well plate "P" can be performed without removing the micro-well plate "P" from the supporting tray. A detailed discussion of dispensing of liquids can be found in U.S. Patent Application Publication No. 2009-0117620-A1 and U.S. Patent Application Publication No. 2009-0117004-A1, both of which were previously incorporated herein by reference.

The components of the system can be controlled by a personal computer using various, available interfaces. These interfaces are identified in FIG. 1. The operations of the magnetic particle processor 10 can be controlled by a personal computer, using commercially available interfaces, which are also identified in FIG. 1. The graphical user interface can use features and controls that are common to modern personal computer graphical user interfaces. For example, drop down menus and tree-views can be used for multiple choices. Radio buttons, checkboxes, and slider controls can provide selection options that are intuitive to the operator. Splash screens, progress bars, and highlighted controls can provide status reports that are intuitive to the operator. Hotlinks can provide access to web sites or local information such as help, maintenance procedures, training, etc.

Figure 7A:
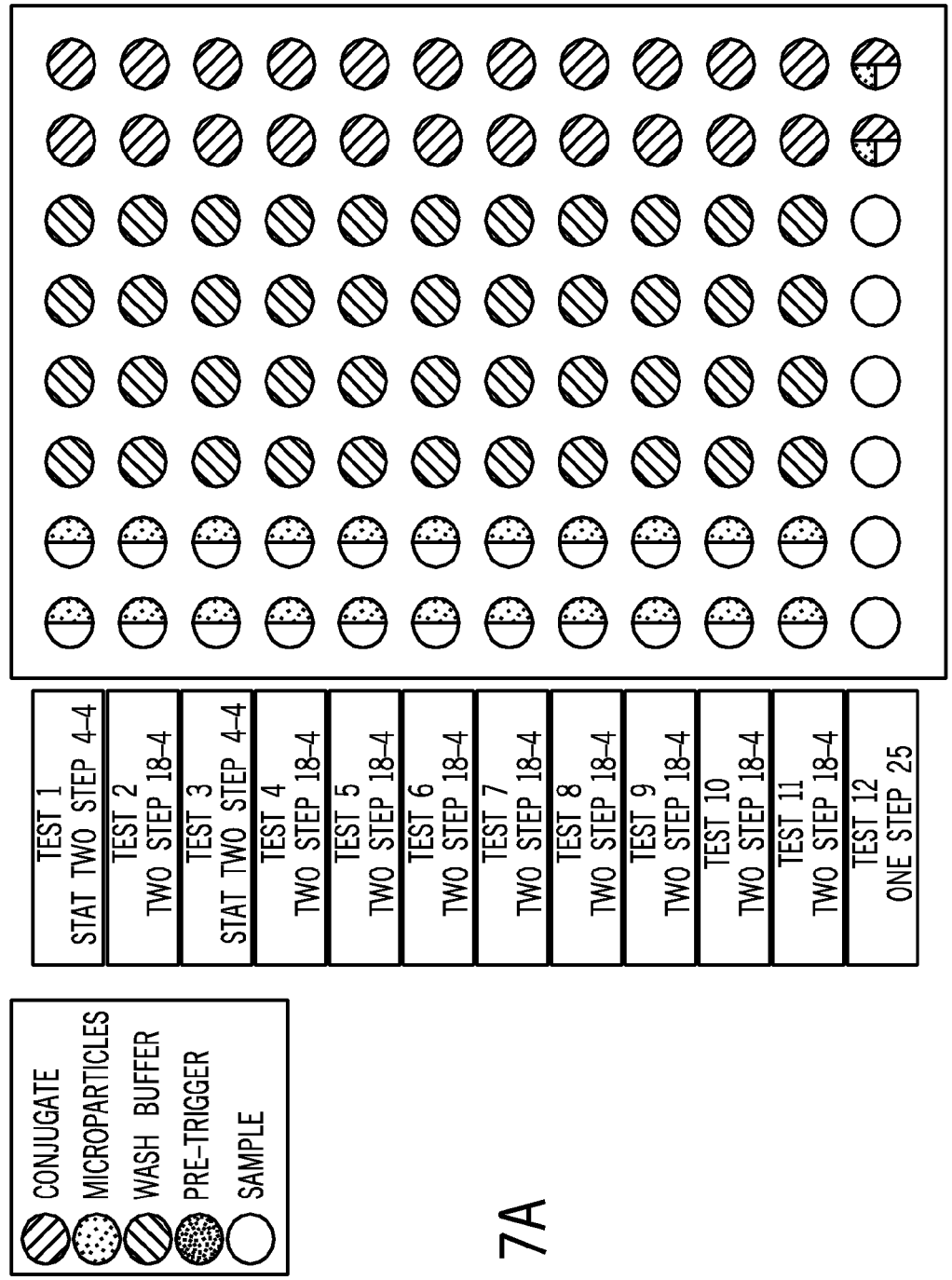
FIGS. 7A and 7B are top plan views of micro-well plates illustrating the kitting of chemiluminescent microparticle immunoassays utilizing two micro-well plates, each micro-well plate having 96 micro-wells. Two rows of micro-wells are processed at a time, and the entire protocol is carried out in two micro-well plates.
Figure 7B:
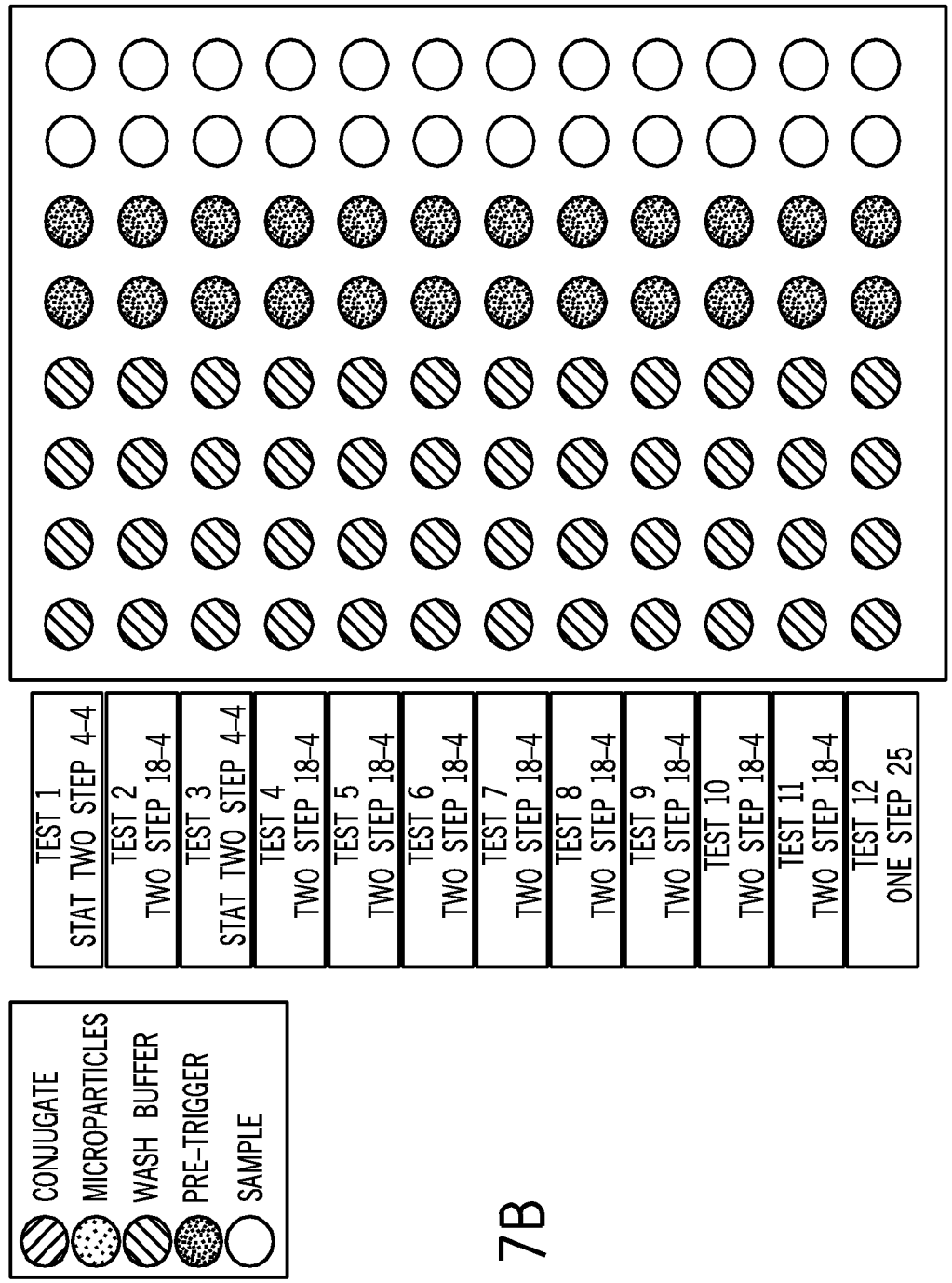
Figure 9A:
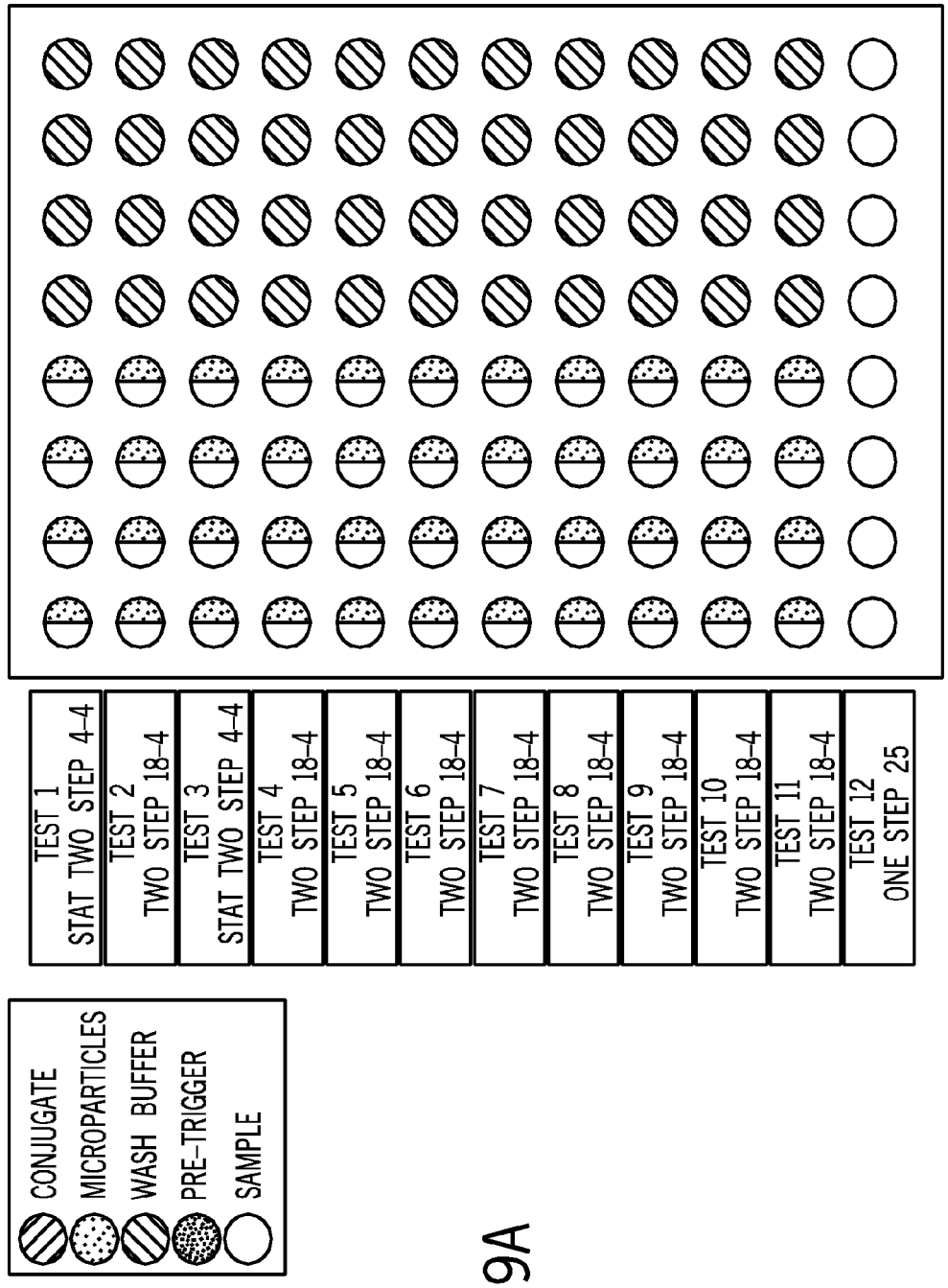
FIGS. 9A, 9B, 9C, and 9D are top plan views of micro-well plates illustrating the kitting of chemiluminescent microparticle immunoassays utilizing four micro-well plates, each micro-well plate having 96 micro-wells. Four rows of micro-wells are processed at a time, and the entire protocol is carried out in four micro-well plates.
Figure 9B:
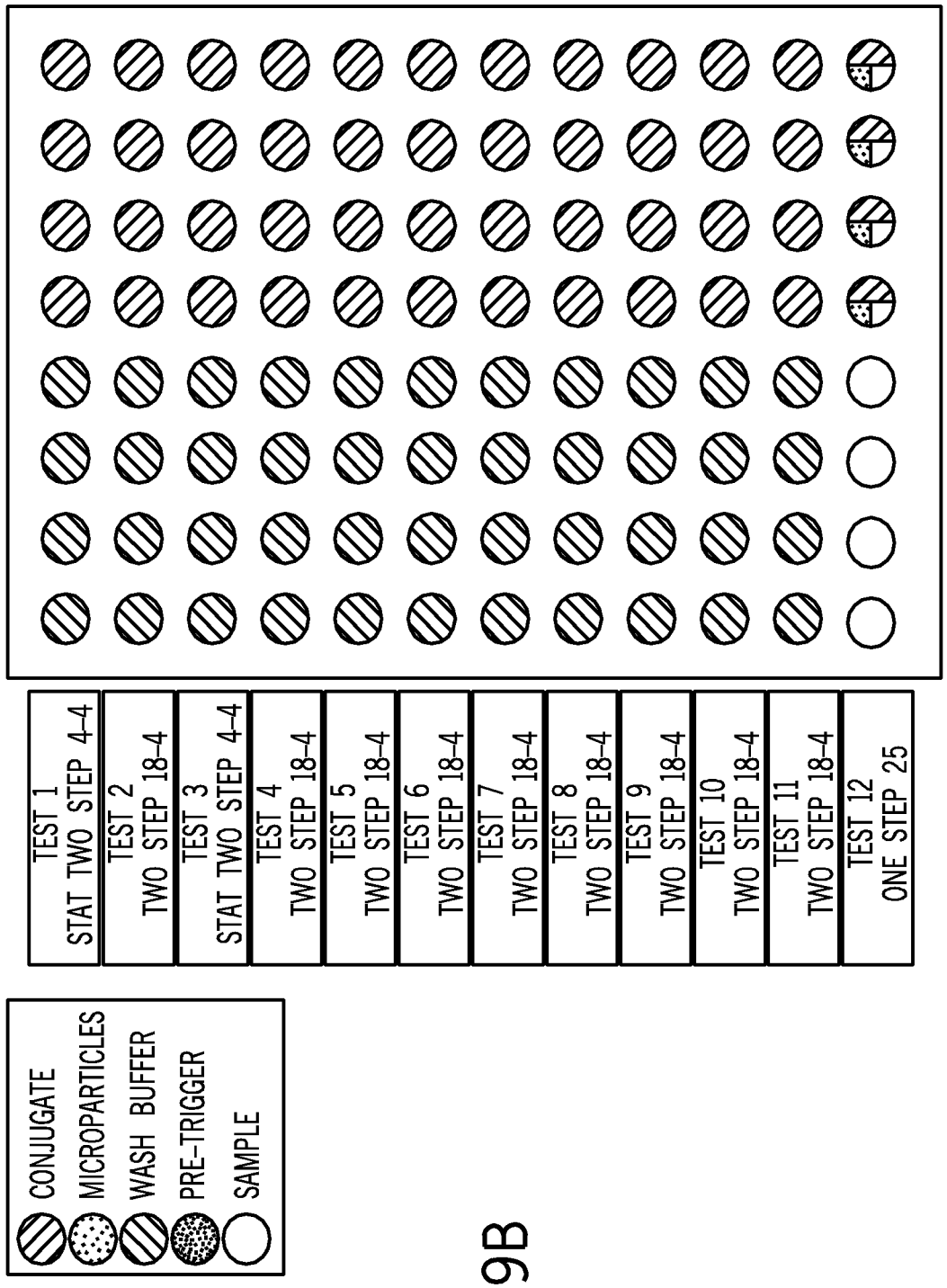
Figure 9C:
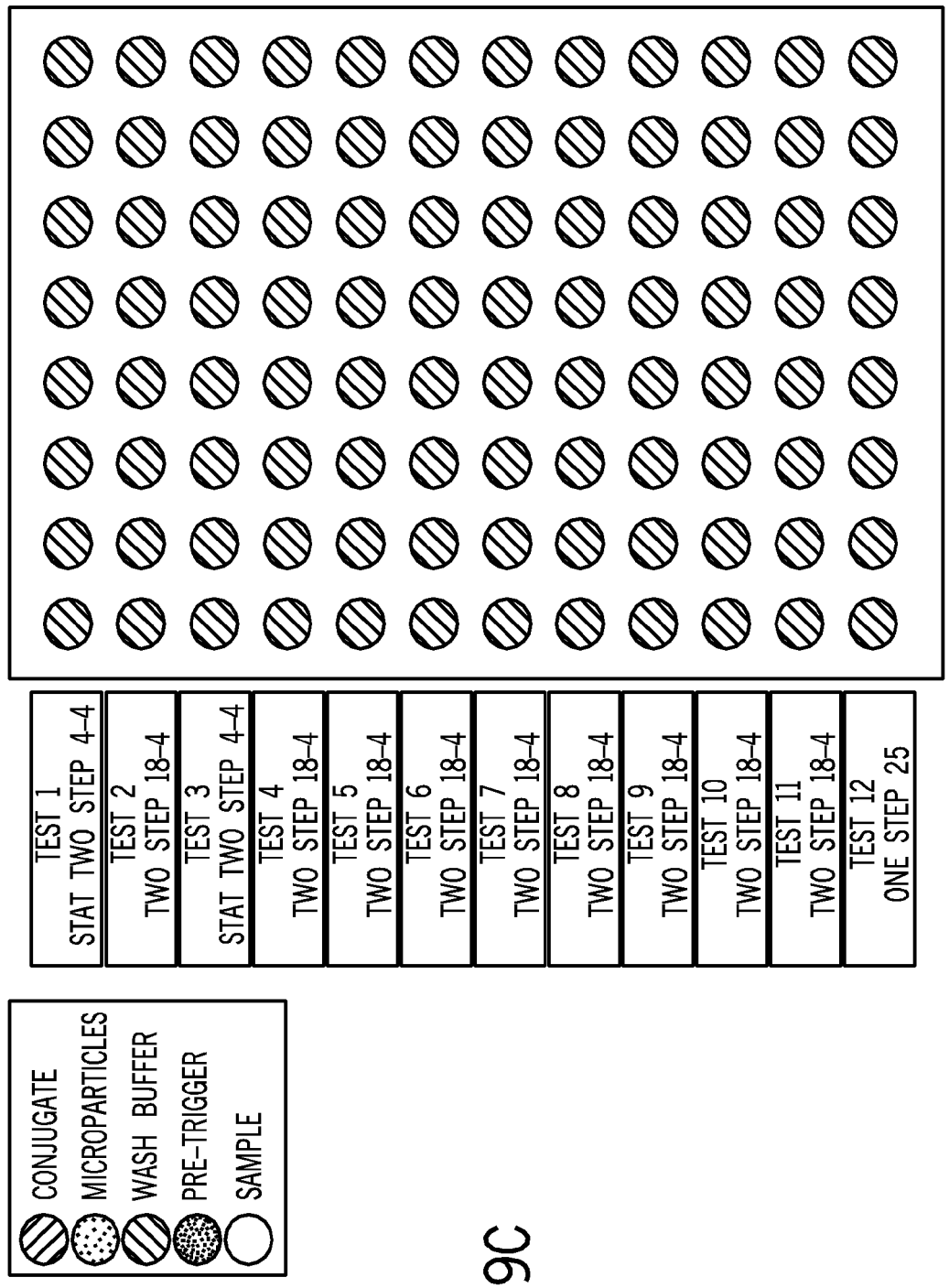
Figure 9D:
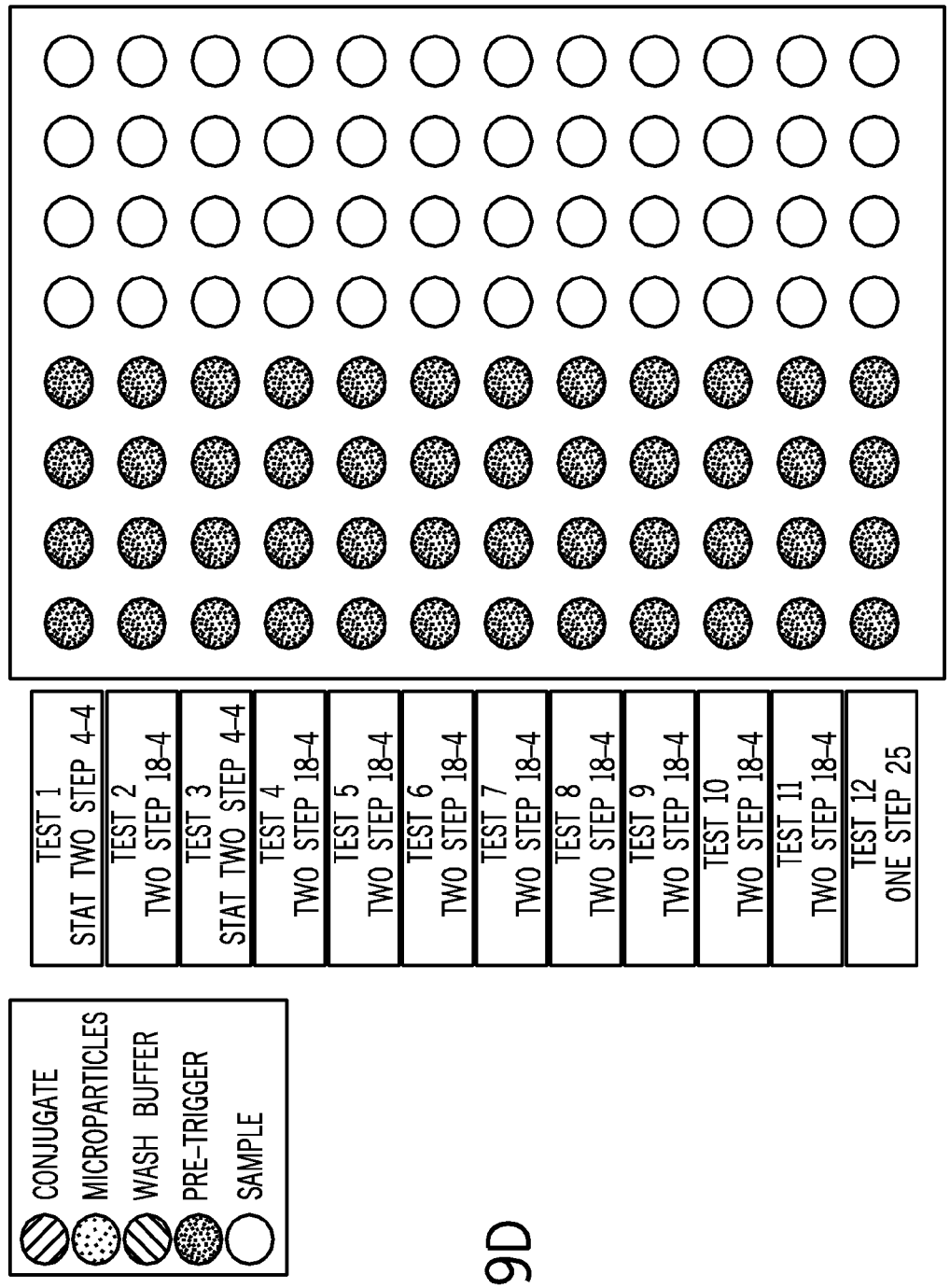

According to the embodiment shown in FIG. 2, one row of magnets per plate, processing of a set of samples requires approximately 30 minutes at a throughput of 24 tests per hour for a batch size of 12 tests. According to the embodiment shown in FIG. 6, two rows of magnets per plate, processing of a set of samples requires 30 minutes. However, 48 tests per hour can be carried out through the use of a batch size of 24 tests. The embodiment shown in FIG. 6 can utilize the kitting arrangement shown in FIG. 7A and FIG. 7B. FIG. 7A and FIG. 7B illustrate the kitting of chemiluminescent microparticle immunoassays utilizing two micro-well plates, each micro-well plate having 96 micro-wells. Two rows of micro-wells are processed at a time, and the entire protocol is carried out in two micro-well plates. According to the embodiment shown in FIG. 8, four rows of magnets per plate, processing of a set of samples requires 30 minutes. However, 96 tests per hour can be carried out through the use of a batch size of 48 tests. The embodiment shown in FIG. 8 can utilize the kitting arrangement shown in FIG. 9A, FIG. 9B, FIG. 9C, and FIG. 9D. FIG. 9A, FIG. 9B, FIG. 9C, and FIG. 9B illustrate the kitting of chemiluminescent microparticle immunoassays utilizing four micro-well plates, each micro-well plate having 96 micro-wells. Four rows of micro-wells are processed at a time, and the entire protocol is carried out in four micro-well plates.

As discussed in United States Patent Application Publication No. 2009-0117004-A1, a synchronization controller is required in order to coordinate the movements of the XYZ aspirating/dispensing device, the inverse magnetic particle processor, and the motor driving the supporting tray in an inverse magnetic particle processor of the type that is equipped with an XYZ aspirating/dispensing device. The supporting tray positions the micro-well plate(s) for the steps of inverse magnetic particle processing. The synchronization controller can be a RS-232 interface for the inverse magnetic particle processor, and a USB interface for the XYZ aspirating/dispensing device. As pointed out in United States Patent Application Publication No. 2009-0117004-A1, micro-well plates can be automatically loaded into the inverse magnetic particle processor and unloaded from the inverse magnetic particle processor by means of gripping devices on the pipettes of the XYZ aspirating/dispensing device.

The operator, or a consultant, reviews the workflow of the laboratory, and then estimates the batch sizes for routine runs, STAT runs, as well as the throughput required for routine runs and STAT runs. The subsystem for magnetic separation and mixing are configured for the batch sizes requested and the quantity of subsystems required to meet the throughput is installed.

The operator or a laboratory information system downloads test orders to the system for samples that will eventually be presented to the system for testing. The operator or laboratory automation system loads the required consumable items onto the system. Consumable items include reagents, diluent, tips, pipette, tip combs, micro-well plates.

Each micro-well in a given row of a micro-well plate "P" contains the same component for inverse magnetic particle processing. For example, kitting micro-well plates for the inverse magnetic particle processor 10 derived from the KingFisher™ 96 magnetic particle processor is carried out a location separate from the magnetic particle processor 10. As stated previously, the samples and the reagents are dispensed into the micro-wells of the micro-well plates "P" at a kitting station, separate from the magnetic particle processor 10. The sample(s), the reagent(s), the buffer(s), and the other materials (e.g., the pre-trigger solution) are added at the kitting station. After the placement of the micro-well plates "P" has been completed, the inverse magnetic particle processing operation is carried out. Additional details relating to incubation can be found in U.S. Patent Application Publication No. 2009-0117620-A1 and U.S. Patent Application Publication No. 2009-0117004-A1, both of which were previously incorporated herein by reference.

Variations in washing can also be carried out by not using certain rows of the micro-well plate, i.e., by filling alternate rows of the micro-well plate with wash buffer material rather than filling adjacent rows of the micro-well plate with wash buffer material. However, such an arrangement could result in lower throughput. In order for this variation to function, certain rows of the micro-well plate are required to be empty so that the non-desired row of magnets will not have any effect on materials in the micro-wells.

Figure 11:
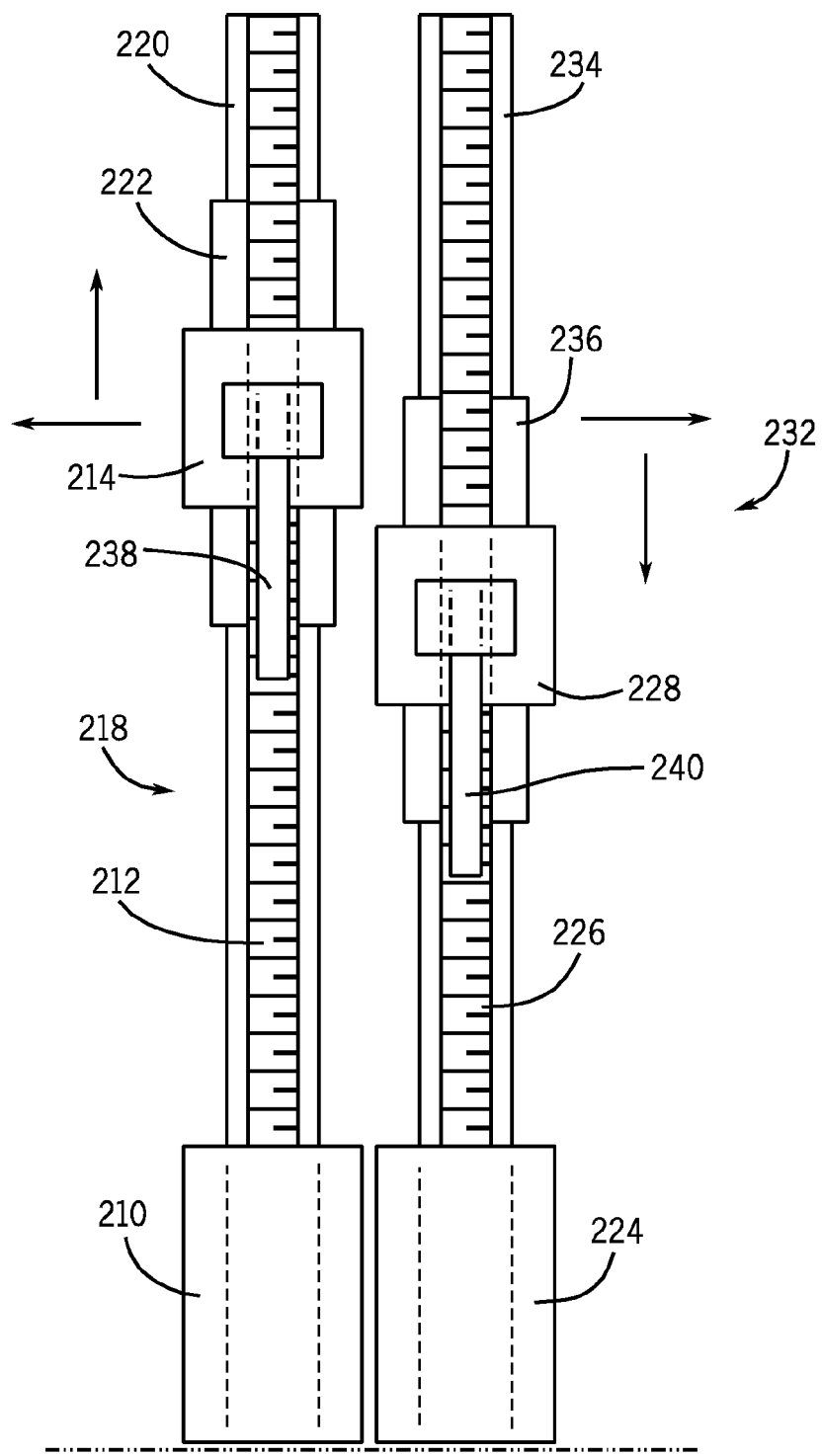
FIG. 11 is a front view in elevation of the inverse magnetic particle processor of FIG. 10. In this view, a first mixing assembly is shown as being adjacent to a second mixing assembly.
Figure 12:
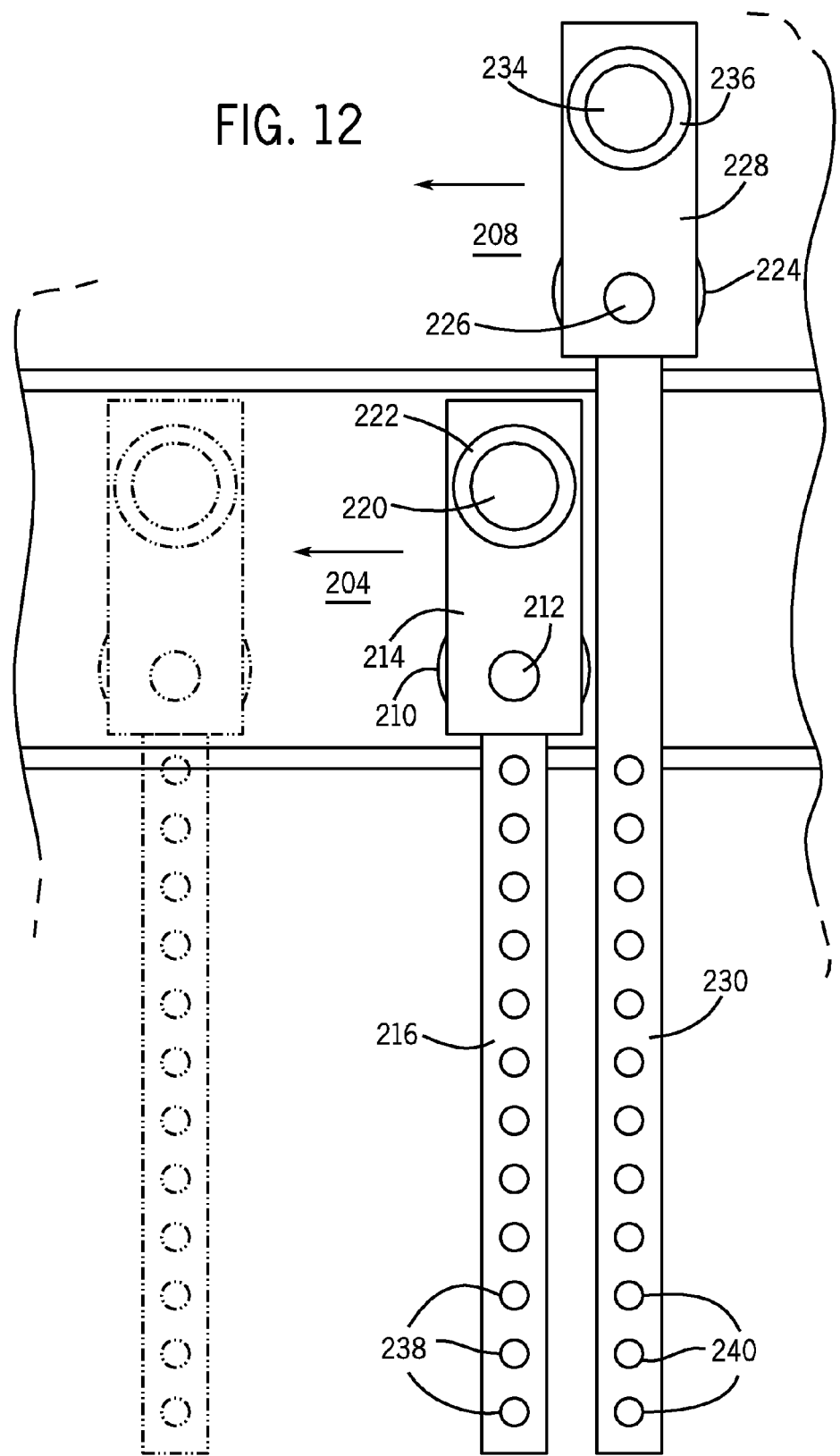
FIG. 12 is a top plan view of the inverse magnetic particle processor of FIG. 10. In this view, a first mixing assembly is shown as being adjacent to a second mixing assembly.

In an alternative embodiment, the magnets can be arranged in rows that move independently of one another. Referring now to FIGS. 10, 11, and 12, an inverse magnetic particle processor 200 comprises a first mixing assembly 202 positioned on a first track 204 and a second mixing assembly 206 positioned on a second track 208. It is preferred that the first track 204 and the second track 208 be offset a sufficient amount so that the first mixing assembly 202 does not interfere with the second mixing assembly 206. However, a plurality of tracks is not required. More than one mixing assembly can be positioned on a given track. It should be noted that if more than one mixing assembly is positioned on a given track, care must be taken so that the mixing assemblies on that track do not collide with each other. The dimensions of the components of the first mixing assembly 202 are similar to or are identical to the dimensions of the components of the second mixing assembly 206. Each mixing assembly can be driven in horizontal directions by means of known driving mechanisms. Such driving mechanisms include, but are not limited to, belt drive mechanisms, chain drive mechanisms, and screw drive mechanisms.

The first mixing assembly 202 comprises a motor 210 that drives a threaded lead screw 212. The threaded lead screw 212 engages a threaded block 214 by which a magnet holder 216 is carried. The threaded block 214 has internal threads that engage the threads of the threaded lead screw 212. As the motor 212 drives the threaded shaft 212, the threaded block 214 slides along a guide 218. The guide 218 comprises a shaft 220 enclosed by a bearing 222.

The second mixing assembly 206 comprises a motor 224 that drives a threaded lead screw 226. The threaded lead screw 226 engages a threaded block 228 by which a magnet holder 230 is carried. The threaded block 228 has internal threads that engage the threads of the threaded lead screw 226. As the motor 226 drives the threaded lead screw 226, the threaded block 228 slides along a guide 232. The guide 232 comprises a shaft 234 enclosed by a bearing 236. Threaded lead screws and threaded blocks can be obtained from or custom made by Nook Industries, Cleveland, Ohio. An on-line catalogue for Nook Industries can be found at www.nookindustries.com, incorporated herein by reference.

Referring again to FIGS. 10, 11, and 12, magnets 238 are positioned in the magnet holder 216. Magnets 240 are positioned in the magnet holder 230. The magnet holder 216 is carried by the threaded block 214. The magnet holder 230 is carried by the threaded block 228. In this arrangement, one row of magnets 238 can be used, for example, to provide vigorous washing. The other row of magnets 240 can be used, for example, to provide moderate washing. Vigorous washing can be effected by operating a row of magnets at a relatively high velocity in the vertical direction. Moderate washing can be effected by operating a row of magnets at a relatively low velocity in the vertical direction. In other words, vigorous washing involves operating a row of magnets at one velocity in the vertical direction, and moderate washing involves operating a row of magnets at a different velocity in the vertical direction. Through the use of this arrangement, every other row of a micro-well plate can be used for different assay protocols. In use, the row of magnets 238 is used for assays set up for rows A, C, E, and G of the micro-well plate. The row of magnets 240 is used for assays set up for rows B, D, F, and H of the micro-well plate.

Referring again to FIGS. 10, 11, and 12, the rows of magnets can be programmed to operate in the manner called for by the magnetic particle processing protocol. Although only two independent rows of magnets are shown, additional independent rows of magnets can be added, so long as the additional mixing assemblies do not interfere with one another.

When magnetic particle processing has been completed, the results derived from the processing are performed by a reader (not shown), e.g., a luminometer in the case of a chemiluminescent microparticle immunoassay. The micro-well plate from which readings are taken is transferred to the reader by means of the XYZ aspirating/dispensing device and any other transfer equipment required, such as, for example, a conveyor belt (not shown) or a robotic mechanism (not shown). The micro-well plates "P" remaining are removed by the XYZ aspirating/dispensing device one at a time and disposed of in a solid waste container (not shown).

The system described herein enables integration of incubation functions with magnetic separation and mixing functions.

The system described herein enables the required control synchronization to be performed via the RS-232 interface on the magnetic separation and mixing subsystem, and the USB interface on the XYZ aspirating/dispensing device.

The operator or laboratory automation system removes the samples from the system.

Magnet holders and tip combs can be exchanged to reconfigure a magnetic separation and mixing subsystem to one, two, or four rows of magnets. Along with layouts for micro-well plates, protocols for micro-well plates, or both layouts and protocols for micro-well plates, subsystem and analyzer throughput can be tailored to the environment of a customer. In addition utilization of micro-well plates can be tailored to the batch size desired by the customer to minimize waste of micro-well plates.

Benefits of the systems described herein include, but are not limited to:
(a) the ability to configure a magnetic separation and mixing subsystem for different throughputs;
(b) the ability to configure different micro-well plate layouts/protocols for different batch sizes to minimize waste of micro-well plates; and
(c) the ability to comprehend protocol changes by interfacing with a XYZ pipetting device and allow new assay protocols, multi-well plate protocols, and protocols requiring fluid dispensing by the XYZ pipetting platform to be interleaved with magnetic separation and mixing operations.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A system for separating a solid magnetic substrate from liquid contents of a reaction vessel, said system comprising
a micro-well plate having a plurality of wells;
a first magnet holder including a first row of magnets to magnetically engage one or more wells;
a second magnet holder including a second row of magnets to magnetically engage one or more wells, wherein the first magnet holder is independently movable relative to the second magnet holder, and wherein the first row of magnets is to move vertically at a first velocity and the second row of magnets is to move vertically at a second velocity;
a first mixing assembly having the first magnet holder coupled thereto; and
a second mixing assembly having the second magnet holder coupled thereto, wherein the first mixing assembly and the second mixing assembly are movable horizontally.

2. The system of claim 1, wherein the first magnet holder includes a plurality of rows of magnets.

3. The system of claim 1, wherein the first and second magnet holders collectively include four rows of magnets.

4. The system of claim 1, wherein the first and second magnet holders collectively include eight rows of magnets.

5. The system of claim 1, wherein the first row of magnets and the second row of magnets are to move in unison.

6. The system of claim 1, wherein the first velocity differs from the second velocity.

7. The system of claim 1, wherein the first velocity and the second velocity are different directions.

8. The system of claim 1, wherein the first magnet holder is vertically movable on the first mixing assembly and the second magnet holder is vertically movable on the second mixing assembly.

9. The system of claim 1, wherein the first mixing assembly is offset laterally from the second mixing assembly.

10. The system of claim 1 further comprising a first track along which the first mixing assembly moves and a second track along which the second mixing assembly moves.

11. The system of claim 1, wherein the first mixing assembly includes a first motor to move the first row of magnets vertically.

12. The system of claim 11, wherein the second mixing assembly includes a second motor to move the second row of magnets vertically.

13. The system of claim 1, wherein the first mixing assembly includes a connector block that is coupled to the first row of magnets and which is to move along a bearing.

14. The system of claim 13, wherein the connector block is to also move along a lead screw.

15. A system for separating a solid magnetic substrate from liquid contents of a reaction vessel, said system comprising, the system comprising:
  a micro-well plate having a plurality of wells;
  a first magnet holder including a first row of magnets to magnetically engage one or more wells;
  a second magnet holder including a second row of magnets to magnetically engage one or more wells, wherein the first magnet holder is independently movable relative to the second magnet holder; and
  an incubator to incubate the first row of magnets for a first duration and to incubate the second row of magnets for a second duration.

16. A system for separating a solid magnetic substrate from liquid contents of a reaction vessel, said system comprising, the system comprising:
  a micro-well plate having a plurality of wells;
  a first magnet holder including a first row of magnets to magnetically engage one or more wells;
  a second magnet holder including a second row of magnets to magnetically engage one or more wells, wherein the first magnet holder is independently movable relative to the second magnet holder; and
  a controller to bypass a wash for at least one of the first row of magnets or the second row of magnets.

* * * * *